United States Patent
Cumming et al.

(10) Patent No.: US 8,100,965 B2
(45) Date of Patent: *Jan. 24, 2012

(54) FLOATING OPTIC ACCOMMODATING INTRAOCULAR LENS

(75) Inventors: J. Stuart Cumming, Laguna Beach, CA (US); Steven J. Dell, Austin, TX (US); Jonathan R. Soiseth, Pomona, CA (US)

(73) Assignee: C&C Vision International Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/762,975

(22) Filed: Apr. 19, 2010

(65) Prior Publication Data

US 2010/0204789 A1 Aug. 12, 2010

Related U.S. Application Data

(63) Continuation of application No. 11/360,019, filed on Feb. 21, 2006, now Pat. No. 7,837,730.

(51) Int. Cl.
*A61F 2/16* (2006.01)

(52) U.S. Cl. ...... 623/6.37; 623/6.38; 623/6.4; 623/6.44; 623/6.46

(58) Field of Classification Search .......... 623/6.37–6.4, 623/6.41, 6.43, 6.44, 6.46, 6.47
See application file for complete search history.

(56) References Cited

U.S. PATENT DOCUMENTS

| | | | |
|---|---|---|---|
| 4,118,808 A | 10/1978 | Poler | |
| 4,122,556 A | 10/1978 | Poler | |
| 4,168,547 A | 9/1979 | Konstantinov et al. | |
| 4,174,543 A | 11/1979 | Kelman | |
| 4,244,060 A | 1/1981 | Hoffer | |
| 4,254,509 A | 3/1981 | Tennant | |
| 4,254,510 A | 3/1981 | Tennant | |
| 4,298,995 A | 11/1981 | Poler | |
| 4,298,996 A | 11/1981 | Barnet | |
| 4,304,012 A | 12/1981 | Richard | |
| 4,409,691 A | 10/1983 | Levy | |
| 4,424,597 A | 1/1984 | Schlegel | |
| 4,441,217 A | 4/1984 | Cozean, Jr. | |
| 4,477,931 A | 10/1984 | Kelman | |
| 4,573,998 A | 3/1986 | Mazzocco | |
| 4,585,457 A | 4/1986 | Kalb | |

(Continued)

FOREIGN PATENT DOCUMENTS

EP 0208546 A 1/1987

(Continued)

OTHER PUBLICATIONS

Archimede Busacca, Ciliary Muscle Physiology Studied by Gonioscopy, Annals of Oculistics, vol. CLXXXVIII, Jan. 1955 (English Translation).

(Continued)

*Primary Examiner* — David H Willse
*Assistant Examiner* — Javier Blanco
(74) *Attorney, Agent, or Firm* — Orrick, Herrington & Sutcliffe, LLP

(57) ABSTRACT

An accommodating intraocular lens comprising a flexible body, a flexible optic which is moveable anteriorly and posteriorly relative to the lens body, and a weakened portion connecting the optic to the body. The body may have extending centration and fixation loops on its distal ends.

2 Claims, 2 Drawing Sheets

U.S. PATENT DOCUMENTS

| | | | |
|---|---|---|---|
| 4,605,411 A | 8/1986 | Fedorov et al. | |
| 4,629,462 A | 12/1986 | Feaster | |
| 4,664,666 A | 5/1987 | Barrett | |
| 4,673,406 A | 6/1987 | Schlegel | |
| 4,704,123 A | 11/1987 | Smith | |
| 4,718,904 A | 1/1988 | Thornton | |
| 4,737,322 A | 4/1988 | Bruns et al. | |
| 4,738,680 A | 4/1988 | Herman | |
| 4,753,655 A | 6/1988 | Hecht | |
| 4,759,761 A | 7/1988 | Portnoy | |
| 4,769,035 A | 9/1988 | Kelman | |
| 4,778,463 A | 10/1988 | Hetland | |
| 4,781,719 A | 11/1988 | Kelman | |
| 4,790,847 A | 12/1988 | Woods | |
| 4,813,955 A | 3/1989 | Achatz et al. | |
| 4,816,030 A | 3/1989 | Robinson | |
| 4,840,627 A | 6/1989 | Blumenthal | |
| 4,842,601 A | 6/1989 | Smith | |
| 4,880,427 A | 11/1989 | Anis | |
| 4,892,543 A | 1/1990 | Turley | |
| 4,919,130 A | 4/1990 | Stoy et al. | |
| 4,932,966 A | 6/1990 | Christie et al. | |
| 4,932,968 A | 6/1990 | Caldwell et al. | |
| 4,932,970 A | 6/1990 | Portney | |
| 4,936,850 A | 6/1990 | Barrett | |
| 4,963,148 A | 10/1990 | Sulc et al. | |
| 4,994,082 A | 2/1991 | Richards et al. | |
| 5,013,322 A | 5/1991 | Rosa | |
| 5,047,051 A | 9/1991 | Cumming | |
| 5,078,742 A | 1/1992 | Dahan | |
| 5,141,507 A | 8/1992 | Parekh | |
| 5,171,319 A | 12/1992 | Keates et al. | |
| 5,171,320 A | 12/1992 | Nishi | |
| 5,217,490 A | 6/1993 | Sayano et al. | |
| 5,376,115 A | 12/1994 | Jansen | |
| 5,476,514 A | 12/1995 | Cumming | |
| 5,496,366 A | 3/1996 | Cumming | |
| 5,522,891 A | 6/1996 | Klaas | |
| 5,578,078 A | 11/1996 | Nakajima et al. | |
| 5,611,968 A | 3/1997 | Grisoni et al. | |
| 5,674,282 A | 10/1997 | Cumming | |
| 5,964,802 A | 10/1999 | Anello et al. | |
| 6,007,579 A | 12/1999 | Lipshitz et al. | |
| 6,051,024 A | 4/2000 | Cumming et al. | |
| 6,193,750 B1 | 2/2001 | Cumming | |
| 6,197,059 B1 | 3/2001 | Cumming | |
| 6,231,603 B1 | 5/2001 | Lang et al. | |
| 6,387,126 B1 | 5/2002 | Cumming | |
| 6,391,056 B2 | 5/2002 | Cumming | |
| 6,494,911 B2 | 12/2002 | Cumming | |
| 6,503,276 B2 | 1/2003 | Lang et al. | |
| 6,524,340 B2 | 2/2003 | Israel | |
| 6,551,354 B1 | 4/2003 | Ghazizadeh et al. | |
| 6,554,859 B1 | 4/2003 | Lang et al. | |
| 6,558,419 B1 | 5/2003 | Pham et al. | |
| 6,638,306 B2 | 10/2003 | Cumming | |
| 6,660,035 B1 | 12/2003 | Lang et al. | |
| 6,749,634 B2 | 6/2004 | Hanna | |
| 6,786,928 B2 | 9/2004 | Callahan et al. | |
| 6,818,158 B2 | 11/2004 | Pham et al. | |
| 6,849,091 B1 * | 2/2005 | Cumming | 623/6.21 |
| 6,881,225 B2 | 4/2005 | Okada | |
| 7,018,409 B2 | 3/2006 | Glick et al. | |
| 7,048,760 B2 | 5/2006 | Cumming | |
| 7,150,760 B2 * | 12/2006 | Zhang | 623/6.37 |
| 7,435,258 B2 * | 10/2008 | Blake | 623/6.37 |
| 2001/0001836 A1 | 5/2001 | Cumming | |
| 2002/0128710 A1 | 9/2002 | Eggleston | |
| 2002/0188351 A1 | 12/2002 | Laguette | |
| 2003/0060880 A1 | 3/2003 | Feingold | |
| 2003/0065387 A1 | 4/2003 | Callahan et al. | |
| 2003/0109926 A1 | 6/2003 | Portney | |
| 2003/0187505 A1 | 10/2003 | Liao | |
| 2004/0002757 A1 | 1/2004 | Lai et al. | |
| 2004/0082994 A1 | 4/2004 | Woods | |
| 2004/0111152 A1 | 6/2004 | Kelman | |
| 2005/0137703 A1 | 6/2005 | Chen | |
| 2006/0020339 A1 | 1/2006 | Ran | |
| 2006/0259140 A1 | 11/2006 | Dell | |
| 2008/0154362 A1 | 6/2008 | Cumming | |
| 2008/0154363 A1 | 6/2008 | Cumming | |

FOREIGN PATENT DOCUMENTS

| | | |
|---|---|---|
| EP | 0336877 A1 | 10/1989 |
| EP | 0941717 A | 9/1999 |
| EP | 1543799 A | 6/2005 |
| FR | 1103399 | 11/1955 |
| GB | 2171912 A | 9/1986 |
| WO | WO 95/06446 | 3/1995 |
| WO | WO 96/15734 A2 | 5/1996 |
| WO | WO 96/25126 A1 | 8/1996 |
| WO | WO 01/97742 A2 | 12/2001 |
| WO | WO 2004/046768 A2 | 6/2004 |
| WO | WO 2006/033984 A1 | 3/2006 |

OTHER PUBLICATIONS

Archimede Busacca, La Physiologid Du Muscle Ciliarire Etudiee par la Gonioscopie, Annales D'Oculistique, vol. CLXXXVIII, 1st Livraison, Jan. 1955 (French Translation).

D. Jackson Coleman, M.D., On the Hydraulic Suspension Theory of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000.

Spencer Thornton, "Accommodating in Pseudophakia," Color Atlas of Lens Implantation, Chapter 25, pp. 159-161.

Lee, Judith, "Update on IOLs," Outpatient Surgery (Mar. 2002), printed Oct. 26, 2004 (http://www.outpatientsurgery.net/2002/os03/f4.shtml).

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbi.nlm.nih.gov/entrez/query.fcgi?cmd=Retrieve&db=pubmed&dopt=Abstract&list...).

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm).

Sabbagh, Leslie, "IOL Design Closes Off PCO," Review of Ophthalmology, printed Oct. 26, 2004 (http://www.revophth.com/index.asp?page=1_255.htm).

* cited by examiner

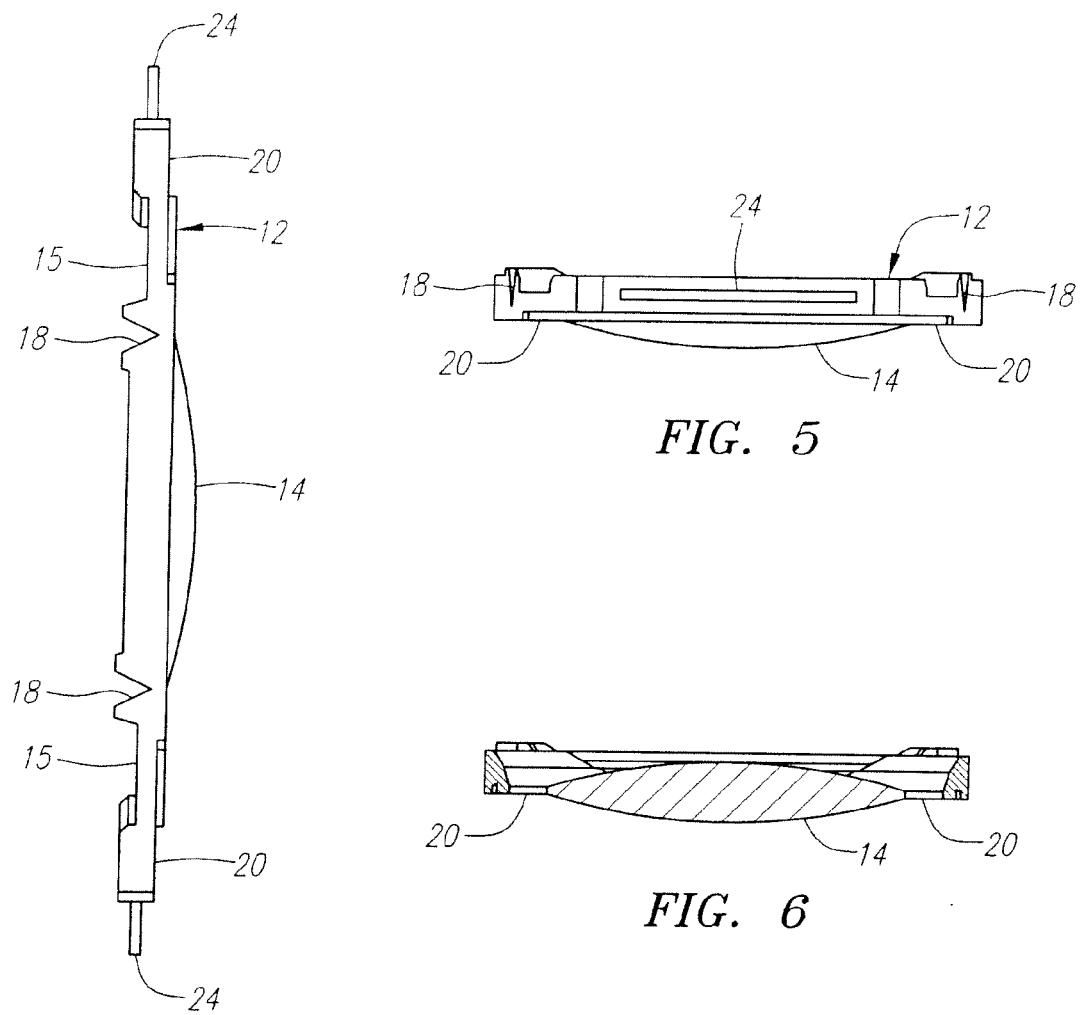
FIG. 4
FIG. 5
FIG. 6
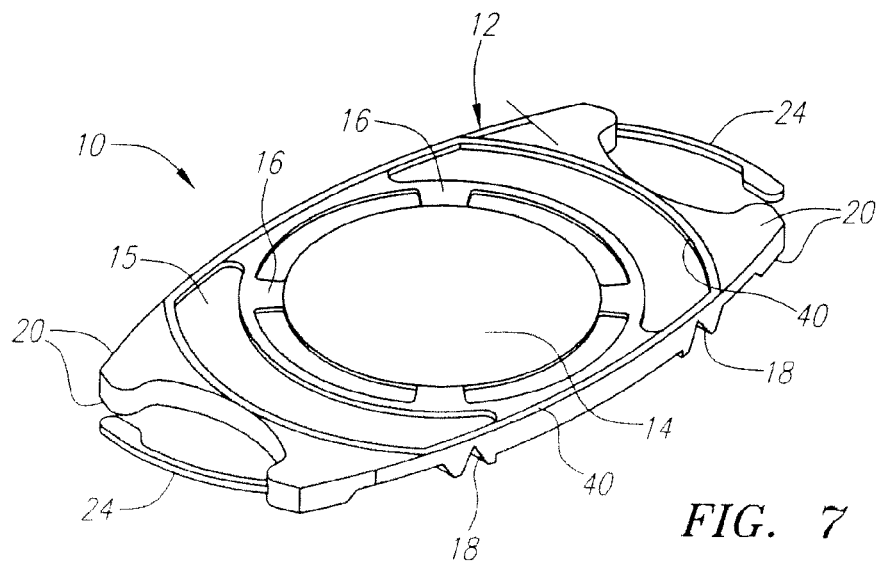
FIG. 7

FLOATING OPTIC ACCOMMODATING INTRAOCULAR LENS

BACKGROUND

This application is a continuation of application Ser. No. 11/360,019 filed on Feb. 21, 2006 now U.S. Pat. No. 7,837,730, all of which is expressly incorporated herein by reference.

Intraocular lenses have for many years had a design of a single optic with loops attached to the optic to center the lens and fixate it in the empty capsular bag of the human eye. In the mid '80s plate lenses were introduced, which comprised a silicone lens, 10.5 mm. in length, with a 6 mm. optic. These lenses could be folded but did not fixate well in the capsular bag, but resided in pockets between the anterior and posterior capsules. The first foldable lenses were all made of silicone. In the mid 1990s an acrylic material was introduced as the optic of lenses. The acrylic lens comprised a biconvex optic with a straight edge into which were inserted loops to center the lens in the eye and fixate it within the capsular bag.

Recently accommodating intraocular lenses have been introduced to the market, which generally are modified plate haptic lenses and, like the silicone plate haptic lenses, have no clear demarcation between the junction of the plate with the optic's posterior surface. A plate haptic lens may be defined as an intraocular lens having two or more plate haptics where combined junctions with the optic represent one quarter or more of the circumference of the optic.

Flexible acrylic material has gained significant popularity among ophthalmic surgeons. In 2003 for example more than 50% of the intraocular lenses implanted had acrylic optics. Hydrogel lenses have also been introduced. Both the acrylic and hydrogel materials are incapable of multiple flexions without fracturing.

The advent of an accommodating lens which functions by moving the optic along the axis of the eye by repeated flexions somewhat limited the materials from which the lens could be made. Silicone is the ideal material, since it is flexible and can be bent probably several million times without showing any damage. Additionally a groove or hinge can be placed across the plate adjacent to the optic as part of the lens design to facilitate movement of the optic relative to the outer ends of the haptics. An example accommodating lens of this nature is disclosed in U.S. Pat. No. 6,387,126 in the name of J. Stuart Cumming.

SUMMARY OF THE INVENTION

According to the present invention a new form of accommodating intraocular lens having a lens body and optic is provided which can be thought of as including a "floating piston optic" with plural straps or fingers, such as four, between the lens body and optic to allow the optic to move anteriorly and posteriorly in a piston fashion in response to the pressure gradient created with accommodation.

Thus, it is a feature of the present invention to provide a new form of accommodating lens.

BRIEF DESCRIPTION OF THE DRAWINGS

FIG. 4 is a side view.
FIG. 5 is an end view.
FIG. 6 is a cross-sectional view along lines 6-6 of FIG. 2.
FIG. 7 is a perspective view of the back or posterior side of the lens.

DESCRIPTION OF PREFERRED EMBODIMENT

Figure 1:
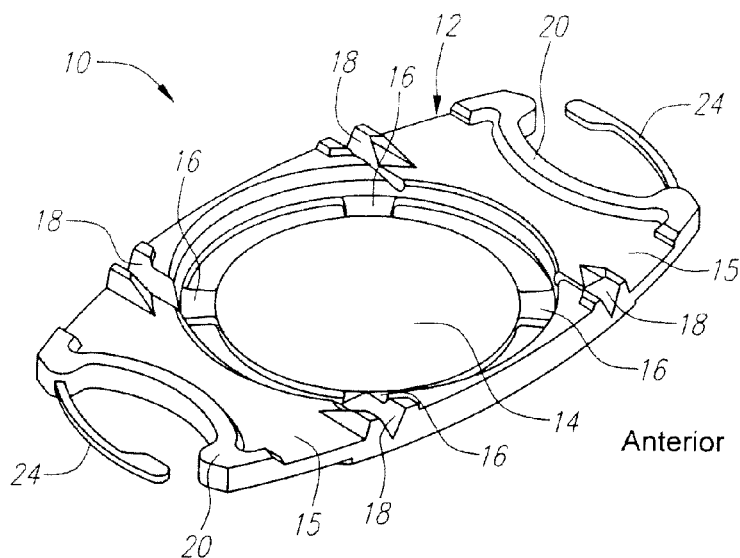
FIG. 1 is a prospective view of the front or anterior side of the lens according to the present invention.

Turning now to the drawings, FIG. 1 is a perspective view of the present lens 10 including a lens body or plate 12 and optic 14. The body 12 includes haptics 15. The body 12 and optic 14 are formed of silicone or other suitable flexible material. Flexible straps 16 are provided between the body 12 and the periphery or outer diameter of the optic 14. The straps may be 0.5 mm long in the radial direction and 0.1 mm thick so as to essentially create an "piston optic" 14 supported by the straps. In yet another iteration the lens may have a continuous skirt surrounding the optic and connecting the optic to the lens body. The optic 14 typically can have a diameter of 4.5 mm, a typical width of the overall lens 10 on the short side is 6.1 mm and the typical length from end to end (not including fixation fingers) on the long side is 10.5 mm.

The body 12 and optic 14, as well as outer thickened footplate ends 20, are formed of silicone or other suitable flexible material. The lens 10 also includes fixation loops 24 of polymide or similar material. A typical outer loop-to-loop length is 11.5 mm. The thickened ends 20 fully engulf the fixation loops 24 in the silicon thus to provide a strong matrix to hold the loops 24. There is an additional function of these thickened areas of the plate. They also serve to elevate the anterior capsule of the human lens away from the optic and from the posterior capsule after the cataract has been removed. This may serve to reduce capsular opacification and contraction.

The straps 16 function as a pseudo-zonular complex, allowing the optic to move anteriorly and posteriorly. The approximately 0.7 mm wide straps are a point of relative weakness in the plane of the lens body 12 encircling the optic 14, thereby allowing the entire optic 14 to herniate forward (anteriorly) from its far posterior position in a translational forward movement. This feature is enhanced by keeping the mass of the optic 14 to a minimum as described below. This new mechanism may boost the effect of the other features of the lens. Rather than a fluid-filled sac pushing through an aperture as in some prior lenses, the present lens involves a deformable solid optic moving anteriorly and posteriorly through a weak area (16) in the plate or body 12. Hinges 18 on the anterior side of the body 12 hinging the haptics 15 further facilitate movement of the optic with ciliary muscle contraction.

Another feature allowing the present lens to accommodate is that the optic 14 can be deformable and constructed with a lower durometer than previously built into any lens. The surrounding plate 12 preferably is made of a higher, standard durometer material, similar to the eyeonics Inc. AT45 lens (which is durometer 48). The optic 14 itself is not required to contribute to the structural stability of the lens and, therefore, the optic 14 can be extremely soft. In addition to forward axial translation, the bending or deformation of the optic 14 with accommodation will induce power change. This may result in the bending of the optic to be accentuated. This feature is further enhanced by maintaining the optic very thin since a thinner optic will bend more than a thick optic for any given level of force applied. An example range of optic 14 center thicknesses is about 0.38 mm to 1.07 mm for a diopter range of 10 to 33. A typical common diopter of the optic of the present lens is 22 diopters and which has a thickness of 0.73 mm. As a comparison, the AT 45 noted earlier in a 22 diopter has a thickness of 0.88 mm, and a newer AT-45SE is 0.98 mm.

A 4.5 mm diameter optic 14 and with a reduced edge thickness of 0.1 to 0.2 mm for example can be provided. The index of refraction can be increased and this will accentuate this feature even further. The fact that this optic 14 is symmetrically tethered to the plate 12 in all meridians by the straps can mean that power changes in the curvature are also symmetrical, meaning spherical power change as opposed to astigmatic changes found in some other lenses. Optic flexure is a new and poorly understood phenomenon, and unwanted optical distortion may be encountered resulting in poor vision either at near or far distances, in which case the durometer of the material will need to be raised.

The present lens can be easily foldable with forceps or an injector. A pre-loaded system is preferable.

Figures 2, 3:
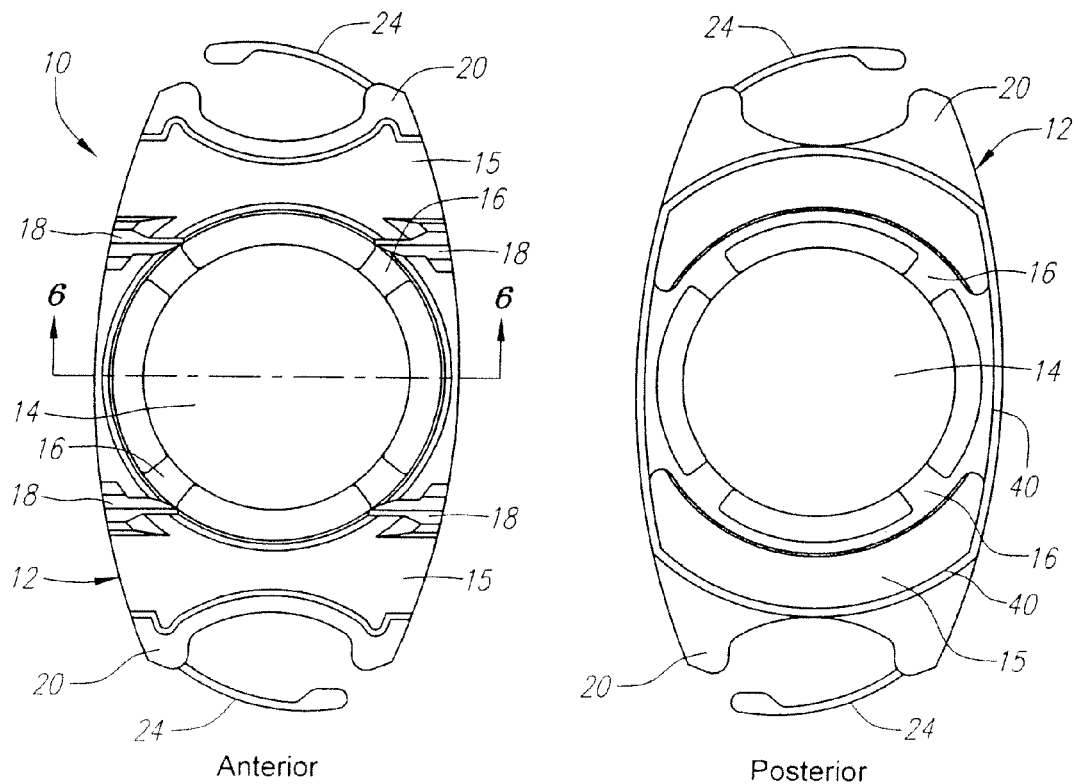
FIG. 2 is a plan view of the anterior side.
FIG. 3 is a plan view of the back or posterior side of the lens.

An additional feature is the incorporation of a ridge or ridges 40 on the back surface (posterior side) of the plate 12 and/or haptic arm as the case may be as seen in FIGS. 3 and 7. These ridges traverse the plate and completely encircle the optic around the perimeter of the lens body. There is an additional ridge central to the first ridge traversing the plate adjacent to the optic straps. The purpose of these ridges is to prevent proliferation of lens epithelial cells into the area behind the plate or optic. For plate lenses this can dramatically reduce the incidence of capsular contraction. Epithelial cells will be prevented from migrating under the plate and undergoing a fibrotic contraction. Furthermore, the square edge of the loops, plate haptics and the square edge of the optic further protect against cells migrating in from the sides of the plate.

While an embodiment of the present invention as been shown and described, various modifications may be made without departing from the scope of the present invention, and all such modifications and equivalents are intended to be covered.

What is claimed is:

1. An uniplanar accommodating intraocular lens comprising an elongated flexible lens body evenly spaced from and completely surrounding and suspending a flexible floating optic for allowing the optic to move anteriorly and posteriorly relative to the body, the elongated flexible body defined by two opposed hinged solid flat haptic plates, the hinges are V-grooves straight across opposite body at the edges of the optic on the anterior side of the lens, the flexible optic being symmetrically mounted to the body by a plurality of thin flexible straps disposed between the periphery of the optic and the lens body adjacent to the hinges, the straps being approximately 0.5 mm long radially and approximately 0.1 mm thick, and the lens body including a plurality of open fixation and centration loops attached to opposite ends of the body, the intraocular lens being designed for the floating optic to move in a piston fashion in response to a pressure gradient created with accommodation, wherein the optic is constructed to optically deform with ciliary muscle contraction to enhance near vision, wherein the lens body has anterior projections to separate the anterior human lens capsule from the lens body, thereby creating a space for the optic to move forward upon ciliary muscle contraction, and wherein the lens body has posterior projections to prevent proliferation of lens epithelial cells into the area behind the optic.

2. An uniplanar accommodating intraocular lens comprising an elongated flexible lens body evenly spaced from and completely surrounding and suspending a flexible floating optic for allowing the optic to move anteriorly and posteriorly relative to the body, the elongated flexible body defined by two opposed hinged solid flat haptic plates, the hinges are V-grooves straight across the body at opposite edges of the optic on the anterior side of the lens, the flexible optic being symmetrically mounted to the body by a plurality of thin flexible straps disposed between the lens body and the periphery of the optic adjacent to the hinges to essentially create a "piston" optic, each strap being approximately 0.5 mm long radially and approximately 0.1 mm thick, and the lens including a plurality of open fixation and centration loops attached to opposite ends of the body, the intraocular lens being designed for the floating optic to move in a piston fashion in response to a pressure gradient created with accommodation, wherein the optic is constructed to optically deform with ciliary muscle contraction to enhance near vision, wherein the lens body has anterior projections to separate the anterior human lens capsule form the lens body, thereby creating a space for the optic to move forward upon ciliary muscle contraction, and wherein the lens body has posterior projections to prevent proliferation of lens epithelial cells into the area behind the optic.

* * * * *